United States Patent
Breen et al.

(10) Patent No.: US 6,848,373 B2
(45) Date of Patent: Feb. 1, 2005

(54) METHOD OF MONITORING HEAT FLUX AND CONTROLLING CORROSION OF FURNACE WALL TUBES

(75) Inventors: Bernard P. Breen, Pittsburgh, PA (US); Robert A. Schrecengost, Beaver, PA (US)

(73) Assignee: Breen Energy Solutions, Pittsburgh, PA (US)

( * ) Notice: Subject to any disclaimer, the term of this patent is extended or adjusted under 35 U.S.C. 154(b) by 128 days.

(21) Appl. No.: 10/372,555

(22) Filed: Feb. 21, 2003

(65) Prior Publication Data

US 2004/0163969 A1 Aug. 26, 2004

(51) Int. Cl.[7] .............................. F23B 7/00; F23N 5/00

(52) U.S. Cl. ..................... 110/341; 110/185; 110/343

(58) Field of Search ................................ 122/392, 379; 374/13, 29, 179, 208; 110/343, 341, 185, 336

(56) References Cited

U.S. PATENT DOCUMENTS

| | | | | |
|---|---|---|---|---|
| 3,274,979 A | * | 9/1966 | Petit | 122/392 |
| 3,276,437 A | | 10/1966 | Jonakin et al. | |
| 4,408,568 A | * | 10/1983 | Wynnyckyj et al. | 122/379 |
| 4,488,516 A | | 12/1984 | Bueters et al. | |
| 4,514,096 A | * | 4/1985 | Wynnyckyj et al. | 374/27 |
| 4,552,098 A | * | 11/1985 | Wynnyckyj et al. | 122/379 |
| 4,571,094 A | * | 2/1986 | Wynnyckyj et al. | 374/29 |
| 4,575,678 A | | 3/1986 | Hladky | |
| 4,722,610 A | | 2/1988 | Levert et al. | |
| 5,139,627 A | | 8/1992 | Eden et al. | |
| 6,485,174 B1 | * | 11/2002 | Albrecht et al. | 374/29 |

* cited by examiner

Primary Examiner—Kenneth Rinehart
(74) Attorney, Agent, or Firm—Buchanan Ingersoll PC

(57) ABSTRACT

In a method of measuring heat flux and corrosion in a furnace, pairs of thermocouples are attached to the back side of the furnace wall. One thermocouple of each pair is attached to a tube and the second thermocouple is attached to a web connected to that tube. A temperature differential is determined for each pair at selected time intervals. A decrease in the difference between temperature differentials indicates slag on the furnace wall has melted indicating corrosion can be occurring.

28 Claims, 4 Drawing Sheets

METHOD OF MONITORING HEAT FLUX AND CONTROLLING CORROSION OF FURNACE WALL TUBES

FIELD OF INVENTION

The invention relates to a method for determining the heat flux incident to a furnace wall of the type having water filled tubes connected by webs that are exposed to combustion products; and subsequently, using these heat flux measurements for determining when slag and corrosion occurs on these furnace walls and taking steps to reduce the corrosion rate and/or to reduce the accumulation of the detrimental slag and fouling deposits.

BACKGROUND OF THE INVENTION

For many years electricity has been produced using boilers or furnaces which generate steam that drives a turbine. Many of the furnaces used to produce electricity have walls formed by laterally adjacent water filled tubes welded together. The tubes may abut one another and be welded together along the line of abutment. Alternatively, the tubes often are connected together by webs, one web between each pair of adjacent tubes. These furnace walls are sometimes called water walls. The water in the tubes is heated by conductive heat transfer. The heated water may reach temperatures of from 700° F. to 1100° F. The water is under pressure and is used to drive a turbine to produce electricity. Depending upon the type of furnace, the water in the tubes may be at pressures of from 2000 pounds per square inch to as high as 5200 pounds per square inch. Most furnaces being used today are operated twenty four hours a day, seven days a week for six to nine months and sometimes 18 months, 24 months or even longer. Then the furnace is shut down for cleaning and routine maintenance. Such maintenance is almost always scheduled in advance to assure that other furnaces are available to supply any needs that may occur during shutdown. Consequently, there is no access to the interior of most furnaces during most of the year.

It is desirable to measure the heat flux into these walls as ash accumulates on them. If the ash remains solid in contact with the wall, it may accumulate, thus effectively insulating the water wall from its heat source and defeating the purpose or efficiency of the boiler. If it melts on the wall, the liquid ash may cause corrosion. When the ash is liquid, it is generally referred to as fused ash, vitrified ash, or most commonly as slag.

Furnace wall tubes are usually made from iron containing metal alloys which often contain 1–5% chromium. During operation of the furnace a protective iron oxide film forms on the fire side surface of the tubes. Ash particles and slag also accumulate on top of the iron oxide film. That slag can be a solution or mixture of iron and silicon oxides, which is commonly identified as $Fe_xO_ySiO_2$. Other chemicals, particularly calcium and aluminum may also be present in the slag. Depending upon oxidizing or reducing conditions and the relative amounts of calcium, iron and silicon present in the slag, and also the presence of potassium and/or phosphate aluminates, the slag will be either liquid or solid at operating temperatures within the furnace.

Until recent years furnace wall tubes corroded slowly because of the protective oxide layer and had a service life of many years, often greater than 20 years throughout the furnace. However, the introduction of low NOx burners has increased the rate of corrosion of these tubes, which can reduce their life expectancy. The result is that not only do tubes have to be replaced, but the corrosion problem has also resulted in the need to improve coal quality, or ash fusion characteristics, sometimes doubling the cost of coal. Consequently, there is a need for a method that will reduce corrosion of furnace wall tubes in boilers. Such a method must first identify when and where corrosion is occurring. Then adjustments can be made to eliminate or reduce the corrosion causing conditions.

Because the water inside tubes is at a high pressure, the tubes could fail if their walls become too thin as a result of corrosion. For this reason, the industry has periodically measured the thickness of the walls of its tubes using sonic measuring techniques and other methods. When these measurements indicate that the walls are becoming too thin, the tubes are replaced. While the industry has been able to determine corrosion rates from periodic measurements of wall thickness, corrosion rates determined in this way are of little use in efforts to control corrosion. That is so because the measurement intervals are such that significant corrosion has occurred between measurements and further this significant corrosion does not shed light on the variation of conditions, mechanisms, coal properties or operating adjustments which cause the significant corrosion.

The corrosion of furnace wall tubes involves several mechanisms. First, removal of the protective oxide film allows further oxidation. Second, if the oxide film is not present or is in an oxidizing-to-reducing transition the iron surface is attacked and pitted by condensed phase chlorides, which may be present. A third mechanism occurs when wet slag runs across the surface of the oxide film. As that happens, iron from the tube goes into the slag solution, particularly when it is in a reducing or oxygen starved condition that can be caused by low $NO_x$ firing. Low fusion calcium-iron-silicate eutectics, alkali iron trisulfates, and sodium vanadates will have formed in the liquid slag. Reduced sulfur in the form of S, $H_2S$, FeS or $FeS_2$ can react with the oxygen of the tube scale depriving the tube metal of its protective layer. Vanadium has different valence states that allow liquid sodium vanadate to react with oxygen from the flue gas. That reaction raises the vanadium oxidation state. Oxygen is deposited on the iron forming rust (FeO, $Fe_2O_3$, $Fe_3O_4$) reducing the vanadium oxidation state. If one could detect when corrosion is occurring, then steps could be taken to stop such corrosion. Yet, prior to the present invention the art has not been able to identify when and where corrosion is occurring while the furnace is in operation. Therefore, it has not been possible to make adjustments to the furnace operation to reduce or stop that corrosion.

Flue gas within the stack as well as flue gas within the furnace is not a homogeneous mixture. The identity and amount of combustion products that are present at any particular time and place in the furnace will typically be different from the identity and amount of combustion products that are present at other places within the furnace or at the same place but at a different time during furnace operation. Consequently, conditions that favor corrosion may be present in some furnace regions but not in others. Hence, corrosion may be occurring on one portion of a furnace wall but not on other portions of the same wall. Frequently, these differences are attributable to the fact that there are several burners in the furnace and one or more burners is operating differently from other burners. If that be true, it should be possible to reduce or eliminate the corrosion by adjusting the operation of one or more burners.

The art has long recognized that slag build-up on furnace walls reduces heat transfer from the combustion chamber to water in the tubes. Therefore, the art has monitored slag build-up and provided soot blowers to remove such build-up during operation of the furnace. Soot blower systems typically use thermocouples to measure furnace wall temperature. Jonakin et al. in U.S. Pat. No. 3,276,437 discloses a soot blower system in which thermocouples can be placed on either side of a furnace tube or web or embedded in the tube or web. Thermocouples are installed at several locations in the furnace wall zone. Temperatures from all thermocouples are periodically read. All readings taken at a given time are averaged and compared to a selected temperature, such as 710° F. When the temperature average is below that selected temperature soot blowers are activated. There is no teaching to measure or use heat flux. U.S. Pat. No. 4,722,610 to Levert et al. discloses a monitor for measuring slag buildup on furnace walls. A monitoring device is placed on the fire side of the water wall. There is a thermocouple within the device and also within the web. U.S. Pat. No. 4,488,516 to Bueters et al. discloses a soot blower system in which slag on furnace walls is monitored using two thermocouples on the fire side. One thermocouple is placed on a web and the second thermocouple is placed on the surface of a tube. None of these patents correlates slag buildup or presence with slag melting and resultant corrosion activity.

Thermocouples are usually installed on the fire side of a furnace wall in one of two ways. One method is to drill a hole through the web between two furnace wall tubes and insert a thermocouple or other temperature probe through the hole. However, drilling holes affects the strength and integrity of the furnace wall. Consequently, furnace owners are reluctant to do that. The art has also placed temperature probes on the inside of the furnace walls without drilling holes through the furnace wall. These probes and the wires running from them are often welded to the wall surface. The thermocouples or other temperature probes must be shielded with an expensive, high temperature, corrosion resistant material such as Hastelloy or Inconel alloys. Even when such shields are provided the temperature probes have a relatively short useful life. When failure does occur the thermocouple usually cannot practically be replaced until the furnace is shut down for scheduled maintenance.

Within the past fifteen years corrosion engineers have developed probes and methods that can monitor corrosion rates in real time as corrosion is occurring in a variety of equipment. These probes and methods are based upon recognition that corrosion is an electrochemical process during which electrochemical activity is generated. Electrochemical noise is a generic term used to describe low amplitude, low frequency random fluctuations of current and potential observed in electrochemical systems. Thus, by placing electrodes in the corrosive environment, one can measure the electrochemical noise that is present. Hladky in U.S. Pat. No. 4,575,678 discloses that measurements of electrochemical noise in corrosive environments can be used to calculate a rate at which corrosion is occurring. He further discloses an apparatus for measuring corrosion that is occurring in a variety of liquid containing apparatus such as pipes, storage tanks, heat exchangers, pumps and valves. Eden et al. disclose a corrosion monitoring apparatus in U.S. Pat. No. 5,139,627 that also relies upon measurements of electrochemical noise. This apparatus has been commercialized by InterCorr International of Houston, Tex., and is being sold under the name SmartCET system. These devices have been used to measure corrosion in storage tanks and pipes. In those environments there is typically one type of corrosion occurring and temperatures seldom exceed a few hundred degrees. For these systems to be used in a furnace it would be necessary to insert the probes through holes drilled in the furnace wall or shield the probes in the same way thermocouples have been shielded. As previously explained, both alternatives have significant shortcomings.

Consequently, there is a need for a method of determining when and where corrosion is occurring on a furnace wall while the furnace is operating. Such a method should permit the operator of the furnace to adjust the operation of the furnace to reduce or eliminate the corrosion which has been identified.

SUMMARY OF THE INVENTION

We provide method of measuring heat flux and resultant corrosion in a furnace of the type having a wall containing a plurality of tubes in which adjacent pairs of tubes are connected by a web or are welded together with the weld bead forming the web. We place a first thermocouple on a back side of one or more tubes which back side is not exposed to heat and products of combustion. A second thermocouple is attached to the back side of a web attached to that tube. We then measure a first heat flux temperature on the back side of the selected tube. We also measure a second heat flux temperature on the back side of the web adjacent to the selected tube. Next, we determine a difference between the first heat flux temperature and the second heat flux temperature. These steps are repeated over time to determine subsequent differences between the first heat flux temperature and the second heat flux temperature. We then compare subsequent differences to at least one previously determined difference. We can decipher that ash has accumulated if the difference has decreased. If we see that a subsequent difference is significantly greater than a previously determined difference we know that the slag has become liquid or fallen off and that corrosion likely is occurring on the tube and furnace wall to which the thermocouples are attached. A comparison is considered significant when the differential between the two compared temperatures is two or more times the lower of the two compared temperature differences.

We prefer to monitor several tube and web locations simultaneously. We further prefer to provide a visual display of the temperature differentials being observed. The display could be a graph for each monitored site. However, when several sites are being monitored we prefer to provide a display corresponding to the furnace wall being monitored. There is a location on the display corresponding to each monitored tube location. A color is applied to each such location of the display to indicate whether or not corrosion has been detected. The display may simply be different colors or a screen containing a picture or illustration of the furnace wall. The screen is able to display different colors in each region of the furnace wall according to whether the temperature differential is normal or indicates liquid slag and potential corrosion.

Other objects and advantages of the invention will be apparent from the description of certain present preferred embodiments thereof which are shown in the drawings.

DESCRIPTION OF THE PREFERRED EMBODIMENTS

The heat flux received by the waterwall tube webbing may be measured as the temperature difference between the center point temperature of the web and the tube water. With adequate casing insulation, the temperature at a selected point on the fire-side of the web will be approximately the same as the temperature at a corresponding point on the insulated back of the web. Since the water in the tube is acting as a heat sink, the temperature on the back side of a tube will be less than the temperature on the front side of the tube during furnace operation. It is possible to determine and illustrate the heat flux lines and temperature lines that occur in furnace walls. An explanation of this phenomenon is import to an understanding of the present invention.

Figure 1:
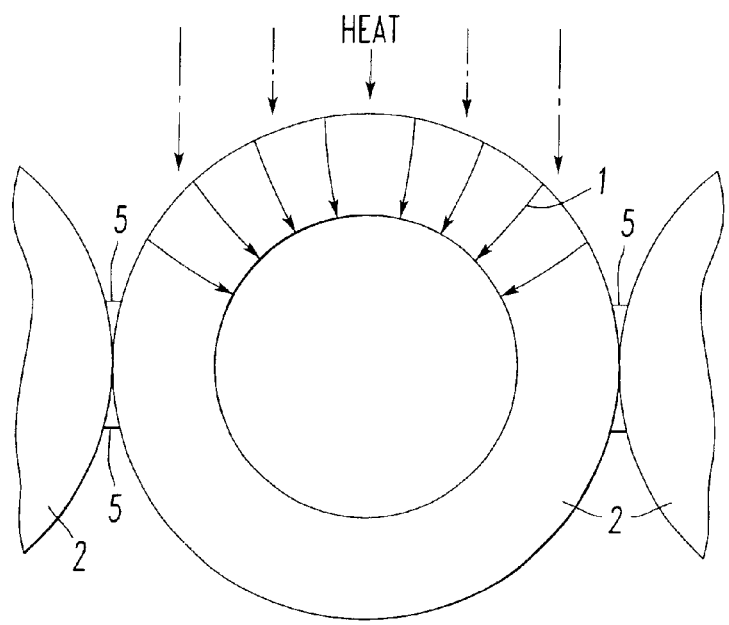
FIG. 1 is a sectional view of a furnace tube and portions of adjacent tubes without an attached web exposed to temperatures during furnace operation with heat flux lines shown in the tube.
Figure 2:
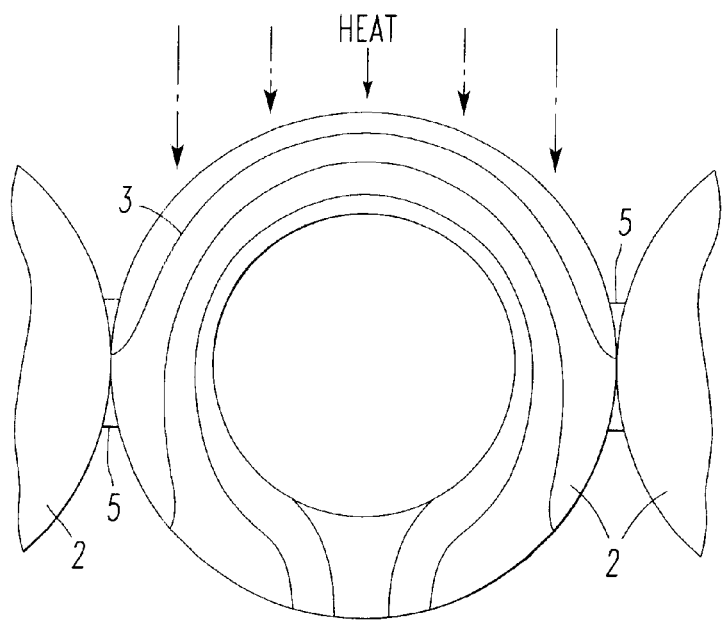
FIG. 2 is a sectional view similar to FIG. 1 of a furnace tube and portions of adjacent tubes without an attached web exposed to temperatures during furnace operation with temperature lines shown in the tube. The heat flux of FIG. 1 flows perpendicular to these lines of temperature, with decreasing temperature lines from the furnace-side to the inner-side of the water filled tube. The perpendicular path forms a temperature gradient which is directly proportional to the magnitude of the heat flux.
Figure 3:
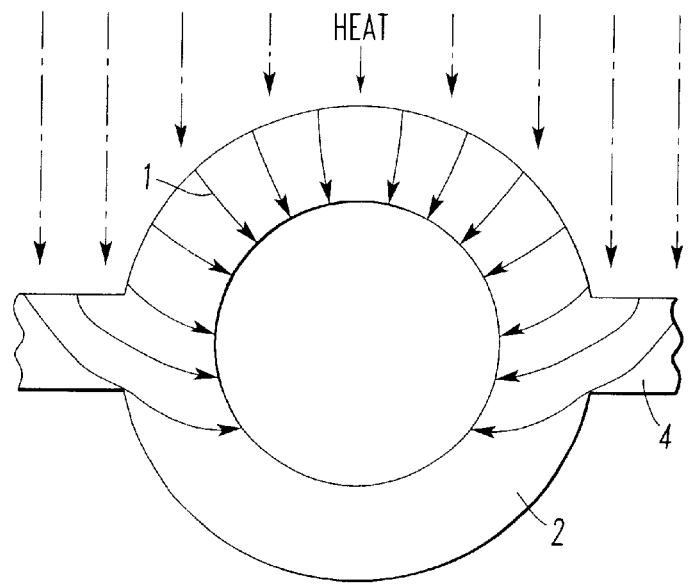
FIG. 3 is a sectional view similar to FIG. 1 of a furnace tube with an attached web exposed to temperatures during furnace operation with heat flux lines shown in the tube. Heat is entering the web and is shown as it flows to the water heat-sink inside the tube.
Figure 4:
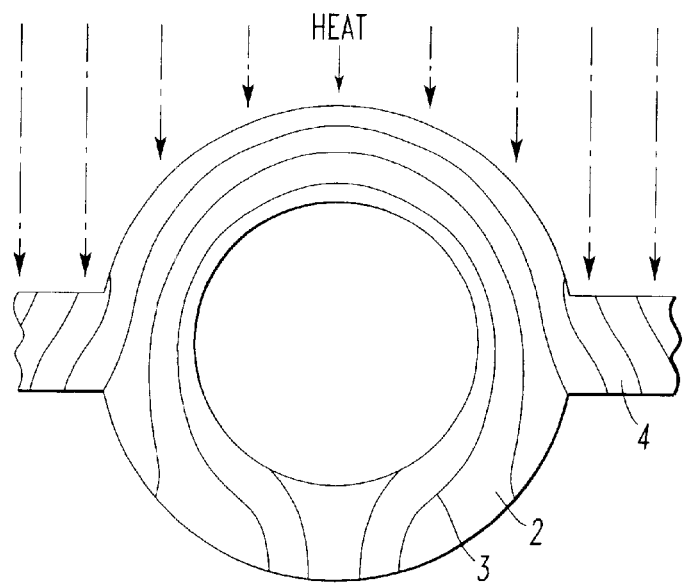
FIG. 4 is sectional view similar to FIG. 2 of a furnace tube with an attached web exposed to temperatures during furnace operation with temperature lines shown in the tube. Heat flux received by the web causes a temperature gradient in the web as the heat flows through the web and into the tube water.

In the furnace walls of FIGS. 1 and 2 adjacent tubes abut one another and are held together by weld beads 5. In the furnace wall of FIGS. 3 and 4 adjacent tubes are separated and connected together by web 4. Referring to FIGS. 1 through 4 there is shown a furnace wall tube 2. The fire-side of each tube is exposed to heat indicated by arrows in the drawings. That heat generates heat flux lines 1 as well as temperature lines 3 in the tube 2. As can be seen from a comparison of FIGS. 1 and 3 and a comparison of FIGS. 2 and 4, the heat flux lines 1 and the temperature lines 3 are different when there is a web 4 between adjacent tubes. But, each pair of weld beads can act like a web. The webbing between waterwall tubes receives a uniform heat flux from the combustion gases which is proportional to projected area. This may be as great as 40% of that incident on the tube projected area. This is indicated by the fact that there are five arrows striking the tube and two arrows striking each web in FIGS. 3 and 4. The incident heat flux is independent of whether or not the tube and web are clean, but build-up will insulate and reduce the heat flux received by the web surface in proportion to of the thickness of the slag. When clean, this 40% heat flux may cause a temperature gradient of 1.4 times that caused by the flux entering the tube surface because both discharge the incident heat to the same heat-sink, the water flow within the tube. However, the web heat flux must also cross 1.5 to 2.0 times the distance on average than the tube heat flux.

The heat flux measured between any two points in the temperature gradient within the metal correlates to the heat flux received from the flames within the hot furnace. The metal tube and tube webbing between tubes make up a serial heat flow path between the high temperature furnace surface (fire-side) temperature and the cooler water-flow inside the tubes (water temperature). The heat flow into the water (or heat flux) is driven by the temperature on the fire side surface. This heat flux is proportional to the temperature difference between any two points within the tube and web heat conducting circuit. By insulating the back-side or the cold-side of the water-wall (routinely done in the interest of efficiency and energy conservation) then the temperature on the back of the tube corresponds closely to the internal water temperature and the temperature on the back of the webbing circuit corresponds to the fire-side surface. That is true because the heat being absorbed must flow into the cooling water and only insignificant heat is allowed to flow out through the back side insulation.

Figure 5:
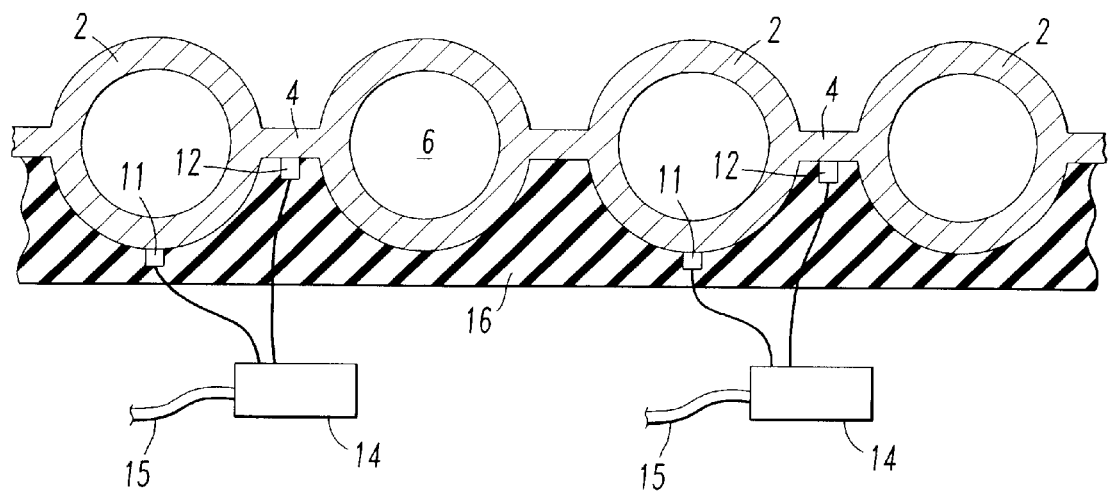
FIG. 5 is top view of a portion of a furnace wall with thermocouples attached in accordance with the present invention.

According to the present invention, thermocouples 11 are attached to the back side of selected furnace tubes as shown in FIG. 5. For each thermocouple 11 a corresponding thermocouple 12 is attached to the back side of a web to which the selected tube is attached. Preferably the thermocouples are centered on the tube and the web. Thermocouple 11 is approximately equidistant from the webs on either side of the tube 2. Thermocouple 12 is approximately equidistant from the tubes on either side of the web 4. Pairs of thermocouples 11 and 12 are placed at selected locations across the furnace wall. For any given furnace wall as many as 50 pairs of thermocouples is used to monitor many selected locations on the furnace wall. Each pair of thermocouples is connected to a comparator device 14 which determines a difference between the temperatures read by the two thermocouples 11 and 12 and generates a signal corresponding to that temperature difference. The signal is then transmitted by cable 15 to a display device or a computer (not shown). Insulation 16 is applied over the back side of the furnace wall to prevent heat loss. Thus, the temperature measured by thermocouple 11 will be very close to the temperature of the water 6 within the tube 2. The temperature measured by thermocouple 12 will be very close to the temperature of the inside of the furnace near the walls. Consequently, there should be a measurable difference, $\Delta T$, between the two temperatures. The temperature measurement is the $\Delta T$ between the back of the centerline of the tube and the back of the centerline of the web. Since these are the same material, the thermocouple circuit can be, but is not necessarily, reduced to a single wire thermocouple at each contact point with the surface. This arrangement of thermocouples is conveniently chosen to be non-invasive and non-intrusive to the heat flux being measured. The thermocouples are placed along the isothermal surface they are intended to measure, in order to improve accuracy and minimize any distortion which they would otherwise cause if they were to cross the zero heat flow insulating plane, thereby short-circuiting the value of the insulation.

The thermocouples allow many points of heat flux from the furnace gases to be monitored simultaneously and continuously with very low cost thermocouple pairs. Each pair represents a temperature driving force proportional to the heat flux entering the fire-side wall at that same locality.

The heat flux decreases as ash accumulates or builds up on the fireside wall. Thus, the deterioration of heat flux as ash accumulates or builds-up can be monitored from point-to-point over time as the heat flux decreases. This is a reliable measurement of furnace wall efficiency for the control of wall-blowing and water-wall water cannons which are designed to remove ash accumulations when they can be detected. However, should the dry ash deposit melt, the heat flux will simultaneously increase. Thus, changes in heat flux can be used to monitor not only ash deposition but also ash melting into wet running slag. The wet slag not only has a higher heat transfer coefficient but is also much thinner than the ash build-up. Also the liquid slag may be at a lower melting temperature than the oxidized ash build-up and thus receives an even greater heat flux from the combustion gases.

The ash fusion temperature is lower in a reducing atmosphere than in an oxidizing atmosphere, and the furnace/boiler design is set so that the ash should remain dry and friable when exposed to oxidizing atmospheres, which after all is the purpose of the fuel combusting furnace, i.e., to combust in oxidizing air. Thus, whenever the ash conditions on the wall become reducing there is a greater tendency for the ash to melt into wet slag. The heat flux measurement device measures this and this can be correlated to increased reducing atmosphere furnace wall corrosion.

Figure 6:
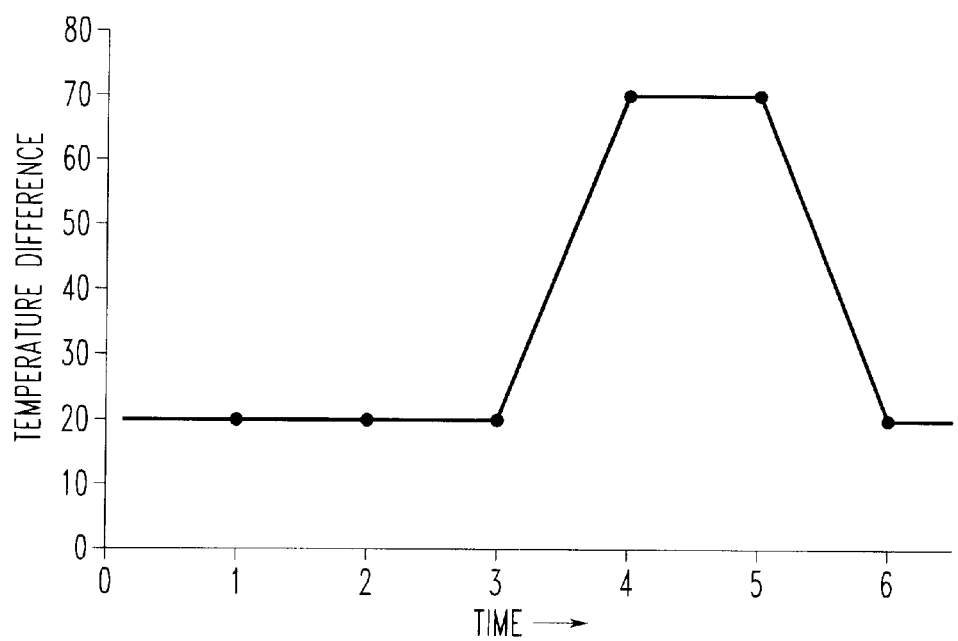
FIG. 6 is a graph of data that would typically be observed when following the method of the present invention.

A typical example of signals received by one pair of thermocouples during operation of a furnace is shown in FIG. 6. A signal corresponding to a temperature difference between thermocouples 11 and 12 is determined at six points in time. Readings taken at times 1 through 3 show a temperature differential of 20°. However, at times 4 and 5 the differential has spiked to 70°. This spike indicates that the slag on the furnace wall in the area being monitored has melted and is now liquid. Since liquid slag indicates corrosion is likely occurring, action is taken between intervals 5 and 6 to change the furnace conditions affecting the area being monitored. Such action may include adjusting a burner or air baffle or even changing the fuel or fuel mixture to a burner. This action causes a change in the flue gas near the arm being monitored. That results in the slag solidifying on the furnace wall. Then the temperature differential drops at interval 6.

Separate graphs like the one shown in FIG. 6 could be constantly generated for every thermocouple pair during operation of the furnace. However, if more than a few furnace wall locations are being monitored the furnace operator could become overwhelmed by the number of graphs being generated. Consequently, we prefer to provide a display such as is shown in FIG. 7 or FIG. 8 to present the data in a more useful format.

Figure 7:
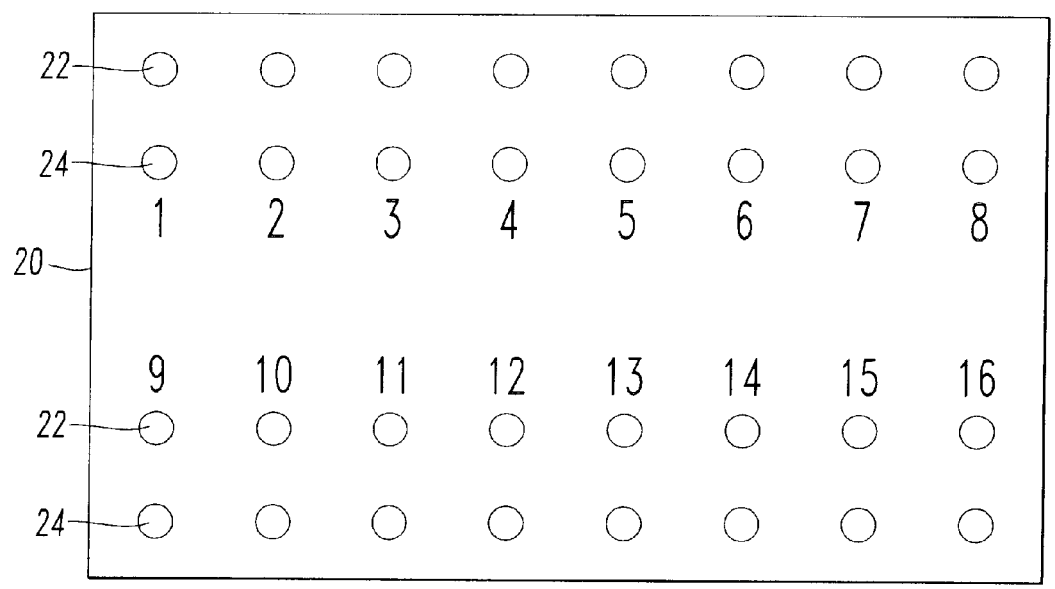
FIG. 7 is a plan view of a display that could be used to report data that would typically be observed when following the method of the present invention.

Referring to FIG. 7 the display is a simple instrument panel 20 containing a pair of LED's 22 and 24 corresponding to each monitored location. Such locations are numbered 1 through 16 on this instrument panel 20. One LED 22 is green and is illuminated when the temperature difference indicates that the slag is in solid form. This LED would be on at time intervals 1, 2, 3 and 6 in the example of FIG. 6. The second LED 24 in each LED pair is red. That LED is illuminated when the temperature difference spikes as occurred during times 4 and 5 in the example of FIG. 6. When the red LED comes on the furnace operator is warned that corrosion is likely occurring in the zone monitored by the thermocouples corresponding to that LED. The furnace operator can then adjust the burners or take other action to stop the corrosion.

Figure 8:
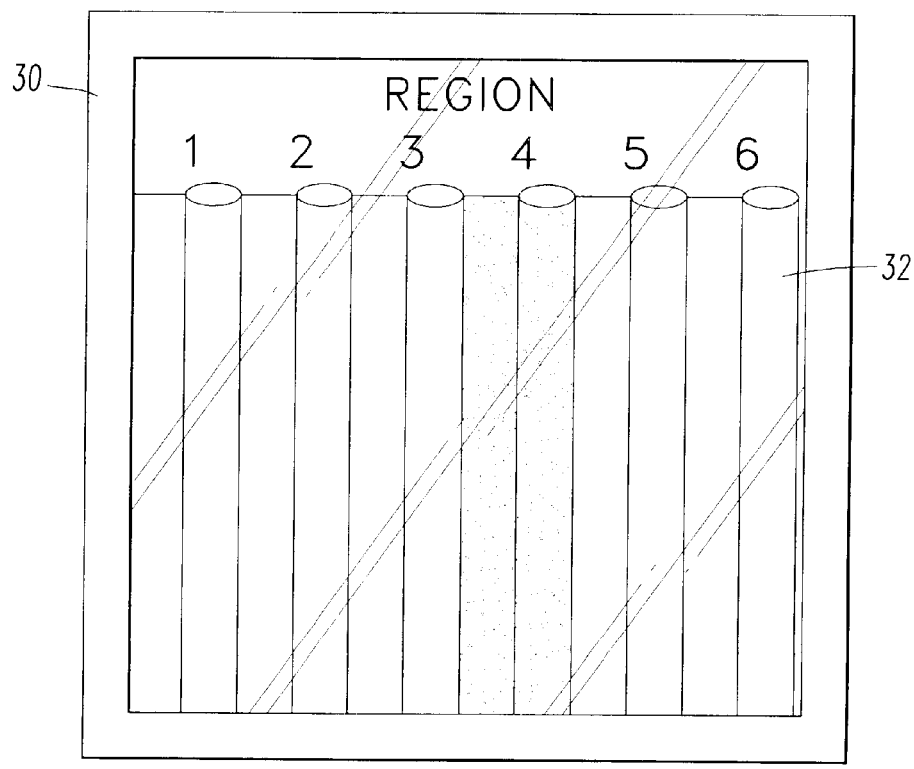

A more sophisticated display shown in FIG. 8 is an LED screen or computer monitor 30 that displays a drawing or other representation 32 of all or a portion of the furnace wall being monitored. In the drawing six monitored portions are represented on the display. Those portions of the furnace wall in which the slag is solid would be shown in one color such as green or blue. Whenever the differential indicates liquid slag on a portion of the furnace wall, the display would show that region of the wall in a different color such as yellow or red. The display in FIG. 8 shows region 4 shaded to indicate that it is a different color from the other sections which are not shaded. This would indicate that the slag is liquid in region 4 of the furnace wall and is solid in the other displayed regions. This type of display could be presented on an LED display, or a computer screen or a CRT monitor.

The data presented in the graph of FIG. 6 or displays of FIG. 7 or 8 could be used to activate an audible alarm whenever the temperature difference is above a predetermined level. In the example of FIG. 6 a computer could be programmed to activate an alarm or command air adjustments whenever the temperature difference was greater than twice the differential of initial start-up of the furnace or was above some selected number such as 40° for the example of FIG. 6.

While the present invention has been described with particular reference to the drawings, it should be understood that the invention is not limited to the preferred embodiments here disclosed but may be variously embodied within the scope of the following claims.

We claim:

1. A method of measuring heat flux and corrosion in a furnace of the type having a wall containing a plurality of tubes, adjacent pairs of tubes connected by a web, a front side of each tube and web being exposed to heat and products of combustion generated in the furnace and a back side of each tube and web not exposed to said heat and products of combustion, the method comprising:

a) measuring a first heat flux temperature on the back side of a selected tube;

b) measuring a second heat flux temperature on the back side of a web adjacent to the selected tube;

c) determining a difference between the first heat flux temperature and the second heat flux temperature;

d) periodically repeating steps a through c to determine subsequent differences between the first heat flux temperature and the second heat flux temperature;

e) comparing subsequent differences to at least one previously determined difference; and f) correlating any increase in compared differences to slag melt and indicative of corrosive conditions in the furnace.

2. The method of claim 1 also comprising adjusting furnace operating conditions whenever corrosive conditions are indicated from the correlating step.

3. The method of claim 1 also comprising presenting a visual display of the difference between the first heat flux temperature and the second heat flux temperature determined at selected time intervals.

4. The method of claim 3 wherein the visual display is one of a graph, an LED display, a display on an LED monitor and a graphic representation of a furnace wall presented on a computer monitor.

5. The method of claim 1 also comprising activating an alarm whenever a subsequent difference is a multiple of a previous difference to which the subsequent difference is being compared.

6. The method of claim 1 also comprising making adjustments to at least one air port in the furnace whenever a subsequent difference is a multiple of a previous difference to which the subsequent difference is being compared.

7. The method of claim 1 wherein the web is formed by weld beads connecting two adjacent tubes forming the furnace water wall.

8. A method of monitoring at least one of heat flux and corrosion activity in a furnace having a wall containing a plurality of tubes, adjacent pairs of tubes connected by a web such that for each tube there is an associated web connected to that tube, each tube and web having a front side which is exposed to heat and products of combustion generated in the furnace and a back side which is not exposed to said heat and products of combustion, the method comprising:
   a) selecting a number of tubes and an associated web for each selected tube;
   b) measuring for each selected tube and associated web a first heat flux temperature on the back side of the tube;
   c) measuring for each selected tube and associated web a second heat flux temperature on the back side of the associated web;
   d) determining a difference between the first heat flux temperature and the second heat flux temperature for each selected tube and associated web;
   e) periodically repeating steps b through d for at least some of the selected tubes and associated webs;
   f) comparing subsequent differences for each of the at least some of the selected tubes and associated webs with previously determined differences for those same selected tubes and associated webs to obtain a differential for each selected tube and associated web; and
   g) displaying at least one such differential.

9. The method of claim 8 wherein the display step comprises creating one of a graph, an LED display, a display on an LED monitor and a graphic representation of a furnace wall presented on a computer monitor.

10. The method of claim 8 wherein the displaying step comprises presenting a display containing a representation of differentials for all selected tubes and associated webs.

11. The method of claim 10 wherein the display comprises a representation of the wall of the furnace and the representation of each differential is a color applied to their presentation at a location on the wall corresponding to a location from which the differential was obtained.

12. The method of claim 8 also comprising correlating any increase in compared differences to slag melt and indicative of corrosion conditions in the furnace.

13. The method of claim 12 also comprising adjusting furnace operating conditions whenever corrosive conditions are indicated from the correlating step.

14. An improved furnace wall of the type having a plurality of tubes, each pair of adjacent tubes connected by a web wherein the improvement comprises a first thermocouple connected to the back side of one tube, a second thermocouple connected to the back side of a web attached to that one tube, and a device connected to the first and second thermocouple which receives signals from the thermocouples and determines a temperature differential between a first temperature corresponding to a signal from the first thermocouple and a second temperature corresponding to a signal received from the second thermocouple.

15. The improved furnace wall of claim 14 also comprising a plurality of thermocouple pairs attached to the furnace wall at selected locations, each thermocouple pair comprised of a first thermocouple connected to the back side of one tube and a second thermocouple connected to the back side of a web attached to that one tube.

16. The improved furnace wall of claim 14 also comprising at least one comparator device which receives signals from at least one thermocouple pair and determines a temperature differential between a first temperature corresponding to a signal from the first thermocouple and a second temperature corresponding to a signal received from the second thermocouple in such at least one thermocouple pair.

17. The improved furnace wall of claim 16 also comprising a display device connected to the comparator device.

18. The improved furnace wall of claim 17 wherein the display device is at least one of an LED display, an LED monitor and a computer monitor.

19. A method of measuring heat flux and corrosion in a furnace of the type having a wall containing a plurality of tubes, adjacent pairs of tubes connected by a web, a front side of each tube and web being exposed to heat and products of combustion generated in the furnace and a back side of each tube and web not exposed to said heat and products of combustion, the method comprising:
   a) measuring a first heat flux temperature on the back side of a selected tube;
   b) measuring a second heat flux temperature on the back side of a web adjacent to the selected tube;
   c) determining a difference between the first heat flux temperature and the second heat flux temperature;
   d) periodically repeating steps a through c to determine subsequent differences between the first heat flux temperature and the second heat flux temperature;
   e) comparing subsequent differences to at least one previously determined difference; and
   f) correlating any increase in compared differences to accumulation of ash or slag deposits on the wall of the furnace.

20. The method of claim 19 also comprising removing ash or slag deposits from the furnace wall.

21. The method of claim 20 wherein the deposits are removed by a soot blower or a water cannon.

22. A method of measuring heat flux in a furnace of the type having a wall containing a plurality of tubes, adjacent pairs of tubes connected by a web, a front side of each tube and web being exposed to heat and products of combustion generated in the furnace and a back side of each tube and web not exposed to said heat and products of combustion, the method comprising:
   a) measuring a first heat flux temperature on the back side of a selected tube;
   b) measuring a second heat flux temperature on the back side of a web adjacent to the selected tube; and
   c) determining a difference between the first heat flux temperature and the second heat flux temperature.

23. The method of claim 22 also comprising:
   periodically repeating steps a through c to determine subsequent differences between the first heat flux temperature and the second heat flux temperature; and
   comparing subsequent differences to at least one previously determined difference.

24. The method of claim 23 also comprising presenting a visual display of the difference between the first heat flux temperature and the second heat flux temperature determined at selected time intervals.

25. The method of claim 24 wherein the visual display is one of a graph, an LED display, a display on an LED monitor and a graphic representation of a furnace wall presented on a computer monitor.

26. The method of claim 23 also comprising activating an alarm whenever a subsequent difference is a multiple of a previous difference to which the subsequent difference is being compared.

27. The method of claim 23 also comprising making adjustments to at least one air port in the furnace whenever a subsequent difference is a multiple of a previous difference to which the subsequent difference is being compared.

28. The method of claim 22 wherein the web is formed by weld beads connecting two adjacent tubes forming the furnace water wall.

* * * * *